United States Patent [19]

Robertson

[11] Patent Number: 5,536,861
[45] Date of Patent: Jul. 16, 1996

[54] MONOMERS FOR PRODUCING ANTIMICROBIAL QUATERNARY GROUP-CONTAINING POLYERS

[75] Inventor: J. Richard Robertson, Alpharetta, Ga.

[73] Assignee: Ciba-Geigy Corporation, Tarrytown, N.Y.

[21] Appl. No.: 270,481

[22] Filed: Jul. 5, 1994

Related U.S. Application Data

[60] Division of Ser. No. 152,888, Nov. 16, 1993, Pat. No. 5,358,688, which is a continuation-in-part of Ser. No. 17,374, Feb. 9, 1993, abandoned.

[51] Int. Cl.$^6$ .................................................. C07F 7/10
[52] U.S. Cl. ........................ 556/419; 556/418; 556/420; 556/425
[58] Field of Search .................................. 556/419, 418, 556/420, 425

[56] References Cited

U.S. PATENT DOCUMENTS

| | | | |
|---|---|---|---|
| 2,976,576 | 3/1961 | Wichterle | 18/58 |
| 3,499,862 | 3/1970 | Wichterle | 269/29.7 |
| 3,503,942 | 3/1970 | Seiderman | 260/80.75 |
| 3,884,886 | 5/1975 | Plueddemann | 526/279 X |
| 4,482,680 | 11/1984 | Sheldon et al. | 525/331.4 |
| 4,615,882 | 10/1986 | Stockel | 424/80 |
| 5,399,737 | 3/1995 | Park et al. | 556/413 |
| 5,461,173 | 10/1995 | Sato et al. | 556/419 X |
| 5,475,124 | 12/1995 | Mazurek et al. | 556/419 |

FOREIGN PATENT DOCUMENTS 0484857  5/1992  European Pat. Off. .

*Primary Examiner*—Paul F. Shaver
*Attorney, Agent, or Firm*—Wenderoth, Lind & Ponack

[57] ABSTRACT

Antimicrobial quaternary ammonium group-containing organosilicon polymers, aqueous disinfectant solutions containing such polymers, and lenses produced from such polymers are provided herein. The polymers are produced by homopolymerizing or copolymerizing, with a suitable comonomer, a quaternary ammonium group-containing organosilicon monomer having, for example, the following structure:

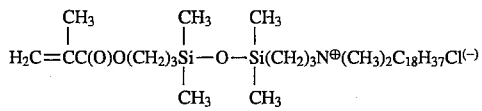

6 Claims, No Drawings

MONOMERS FOR PRODUCING ANTIMICROBIAL QUATERNARY GROUP-CONTAINING POLYERS

This is a divisional application of U.S. application Ser. No. 08/152,888, filed Nov. 16, 1993, now U.S. Pat. No. 5,358,688, which is in turn a Continuation-In-Part of now abandoned application, Ser. No. 08/017,374, filed Feb. 9, 1993.

BACKGROUND OF THE INVENTION

1. Field of the Invention

This invention relates to quaternary ammonium group-containing organosilicon polymers and novel monomers used to produce these polymers. The invention also relates to methods of producing such polymers and monomers. The polymers may be used in wide applications as antimicrobial agents as, for example, in solutions to disinfect contact lenses and certain of these polymers may be used to produce solid structures, such as contact lenses.

2. Prior Art

Contact lenses are typically made of hydrophilic and partially hydrophilic plastic materials. These materials have a high capacity to absorb water and swell to a soft mass or hydrogel. This hydrogel is characterized by excellent mechanical properties, complete transparency, good shape retention and high resistance to degradation in boiling water. Such hydrophilic or partially hydrophilic plastic materials are described in such patents as U.S. Pat. Nos. 2,976,576, 3,499,862 and 3,503,942. These patents disclose, inter alia, the production of the so-called soft contact lenses.

One of the problems associated with cleaning soft contact lenses made from the aforementioned hydrophilic materials, is in the disinfecting and cleaning of such lenses. These lenses have a high capacity to absorb water, i.e. upwards of about 38 weight % water, based on the total weight of the hydrogel. Therefore, the compounds employed to disinfect the contact lenses are often absorbed and possibly even concentrated in the lenses and later released when the soft contact lenses are worn on the eye. This, of course, may damage or stain the contact lenses and harm the sensitive tissues of the eye. Such preservative or disinfectant materials typically used to disinfect the contact lenses may be such materials as chlorohexidine or thimerosal, for example.

To overcome these problems, materials such as quaternary ammonium group-containing polymers having antimicrobial activity may be used to disinfect the lenses. The advantage of using antimicrobial polymers is that they have a larger molecular size and are less likely to penetrate or be absorbed into the soft contact lenses, and tend to be less toxic.

Examples of such polymers are the polymeric quaternary ammonium compounds having recurring vinyl benzene ammonium units. Such polymers are disclosed in U.S. Pat. No. 4,482,680. These polymers have a disadvantage in that they have relatively poor solubility in water.

Another example of polymers employed for disinfecting contact lenses are the organosilicon quaternary ammonium compounds disclosed in U.S. Pat. No. 4,615,882. These polymers are produced by reacting an organosilicon quaternary ammonium salt having a hydrolyzable group with a water soluble high molecular weight organic polymer, such as polyvinyl alcohol, reactive with said hydrolyzable group. The hydrophilic polymers described in U.S. Pat. No. 4,615,882 have silicone and quaternary ammonium components as required in the present invention, however the synthesis of the polymers disclosed in the patent result in the formation of hydrolytically unstable linkages, e.g. silicon-oxygen-carbon linkages. The existence of such Si—O—C bond is unstable, breaks down over time, and could lead to toxicity problems.

SUMMARY AND OBJECTIVES OF THE PRESENT INVENTION

The present invention relates to quaternary ammonium group-containing organosilicon polymers having antimicrobial activity which do not have the unstable linkages, i.e. the silicon-oxygen-carbon linkages of U.S. Pat. No. 4,615,882 and therefore are free of the toxicity problems due to the breakdown of these compounds with time.

The antimicrobial polymers of the present invention are suitable for treating soft contact lenses and are especially suitable for cleaning and disinfecting such lenses to remove proteinaceous deposits which tend to form and build on the lenses during wear and handling.

The polymers of the present invention are of such a molecular size that they do not penetrate the contact lenses polymer matrix as readily as non-polymeric organic molecules, and when they do penetrate, are less toxic than said non-polymeric compounds. Therefore, they are less apt to damage the lenses or injure the eye as is typical of non-polymeric materials which penetrate the lenses and may leach out and damage the soft tissues of the eye during the use thereof.

The organosilicon quaternary ammonium compounds of the present invention may typically be dissolved or dispersed in a solution, especially an aqueous solution, used to disinfect the contact lenses and are used in amounts sufficient to disinfect the lenses. The polymers of the present invention have advantages over the poly(vinylbenzyl quaternary ammonium) halide structure disclosed in the Sheldon patent, U.S. Pat. No. 4,482,680 in that they are more water soluble and therefore can be more easily dissolved in aqueous solutions. The solutions, according to the present invention, are preferably aqueous based solutions, occasionally containing organic solvents, which are nontoxic to the eye, i.e. are ophthalmically safe for use.

Although the quaternary ammonium-containing organosilicon compounds of the present invention are especially suitable for disinfecting soft lenses, they can also be used for other utilities where the antimicrobial properties are effective, i.e. for hair care and in other topical pharmaceutical products. Specific uses may be in the therapeutic skin care preparations and use as deodorants or antimicrobials for the body, etc. In addition, the products can be formulated with various cleanser components to form disinfectants for home or hospital use.

DETAILED DESCRIPTION OF THE INVENTION

The quaternary ammonium group-containing organosilicon polymers of the present invention can be produced by homo or copolymerizing a monomer or compound of the following generic structure:

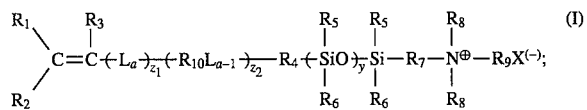

wherein $R_1$, $R_2$ and $R_3$ are independently H, $C_{1-7}$alkyl, or —COOR$^{13}$ with R$^{13}$ being H or $C_{1-4}$ alkyl;

$Z_1$ and $Z_2$ are independently 0 or 1;

-continued
3-methacryloxypropyltetramethyldisiloxanylpropyldimethylocta-
decylammonium chloride (MADAC)

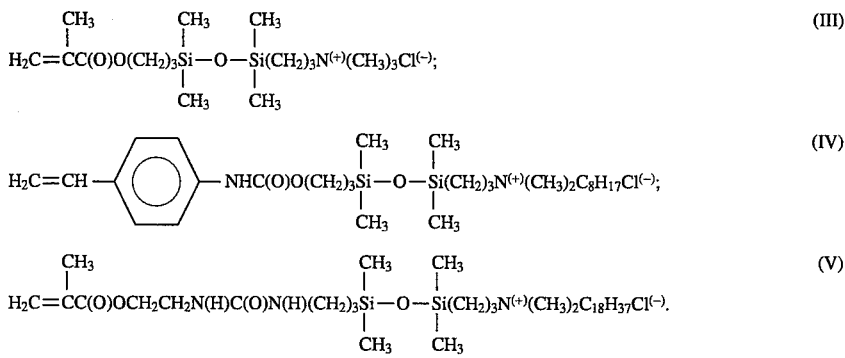

$L_a$ is

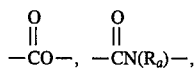

or a direct bond;

$L_{a-1}$ is a direct bond,

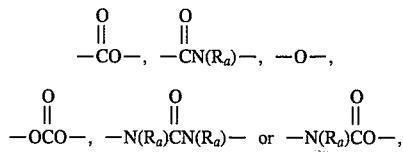

wherein $R_a$ is H or $C_1$–$C_8$ Alkyl;

$R_{10}$ is $C_{1-20}$aliphatic, $C_{1-25}$ cycloaliphatic or $C_{1-20}$ aryl, each of which may be substituted with up to five halogen atoms, or $(CH_2CH(R_a)O)_j$ where j is from 1 up to 50 and wherein $R_a$ is as defined above.

$R_4$ and $R_7$ are independently $C_{2-10}$ aliphatic, $C_{2-8}$ alkylene, $C_{1-4}$ alkylene-(oxy-$C_{1-4}$ alkylene)$_g$, $C_{1-4}$ alkylene(-)$OCH_2$-(hydroxy $C_{1-4}$ alkylene)-$CH_2$, cycloaliphatic up to 25 carbon atoms or aryl up to 25 carbon atoms, wherein g is an integer from 1 to 10;

y is an integer of 1 to 10;

$R_5$ and $R_6$ are independently $C_1$–$C_8$ alkyl, $C_6$–$C_{25}$ aryl, or $C_6$–C25 cycloaliphatic which may be substituted by one or more halogen, hydroxy, $C_{1-4}$alkyl, carboxy or $C_{1-12}$ perhaloalkyl groups and $R_5$ or $R_6$ may be —$Si(OSiCH_3)_3$;

$R_8$ and $R_9$ are independently $C_1$–$C_{24}$ alkyl, $C_{2-24}$ Alkenyl, $C_3$–$C_{24}$ cycloaliphatic and $C_{6-25}$ aryl, which groups may be each substituted with from 1–11 groups selected from hydroxy, $C_{1-4}$ alkyl, carboxy, $C_{1-12}$ perhaloalkyl or halogen and $R_8$ and $R_9$ may also be $(CH_2CH_2O)_xH$, where x is from 1 to 10 units, and X is an ophthalmically acceptable counterion.

The ophthalmically acceptable counterion is preferably a halogen, hydroxy, acetate, $SO4^{-2}$, $CO3^{-2}$, or $PO4^{-2}$ for example. The cycloaliphatic groups are all preferably groups containing 6 to 10 carbon atoms, and more preferably 5 to 7 membered cycloaliphatic groups.

Typical structures of the above monomers are as follows:

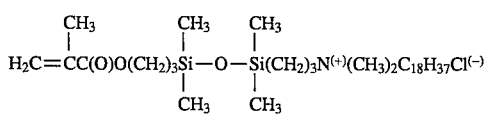

The monomers of the present invention used to produce the organosilicon polymers are novel and a description of a typical procedure for producing these novel monomers is reproduced below.

Production of the Quaternized Organosilicon Monomer of the Present Invention Below is a synthetic scheme for the production of the MADAC monomer of the formula (II) (a typical and preferred monomer) used in producing the water soluble polymers and contact lens materials of the present invention.

Step 1

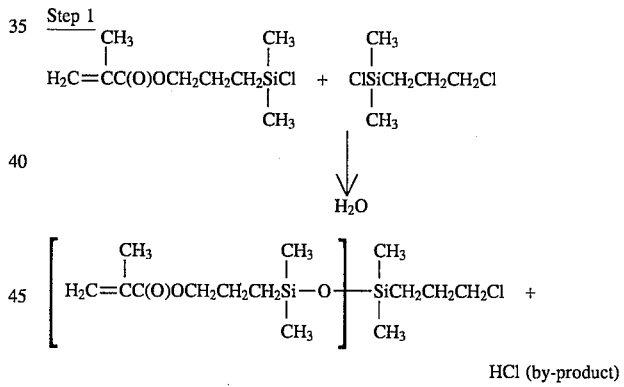

HCl (by-product)

R—L represents structure in brackets.

Step 2

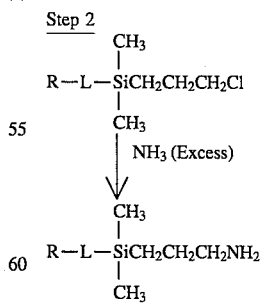

Step 3

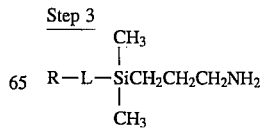

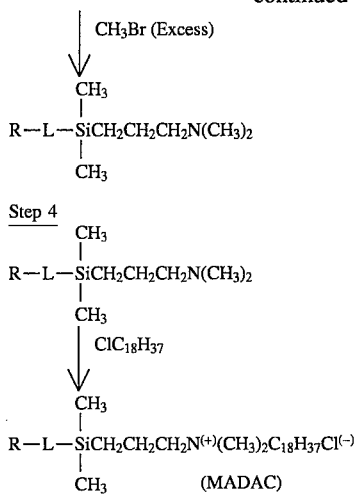

Reaction Conditions for Producing the Monomer

The reaction in Step 1 may be varied, but is usually carried out preferably from about ambient temperatures to about 40° C. in an aqueous solution, which may be slightly acidic.

The reaction with the amine in Step 2 is carried out in an aqueous solution at a temperature from about 0° C. up to ambient temperatures and preferably from 0° C. to about 20° C. This reaction is ordinarily carried out at atmospheric pressure, however, it can be carried out under high pressure at even higher temperatures, if necessary.

Step 3 is preferably carried out at a reaction of from about room temperature to up to about 40° C. in a suitable organic solvent, especially an inert organic solvent, such as toluene, benzene, etc.

Step 4 may be carried out in a solvent, preferably at room or ambient temperature. The solvents include such organic solvents as toluene, benzene and other inert, typically used solvents. The reaction conditions vary depending upon the nature of the reactants, solvents employed, pressure conditions, etc. The above conditions represent the typical conditions employed.

The other monomers of the generic formula (I) can be produced by following the same reaction scheme used to produce the MADAC monomer as set forth in Steps (1) to (4) above.

PREPARATION OF POLYMERS

The quaternized monomers of the generic formula (I) set forth above, may be homo-or co-polymerized to produce the final polymer structure. The monomers are typically polymerized in an inert atmosphere, such as nitrogen or argon, free of oxygen. The polymerization may be initiated by way of initiators, such as peroxides or azobisisobutyronitrile (AIBN) in amounts sufficient to initiate the reaction, i.e. typically from about 0.01 to 0.5 weight % based on the weight of the monomer. The reaction may be carried out in the presence of a solvent, such as an alcohol, toluene, benzene, tetrahydrofuran or various ketones, such as methylethyl ketone. The reaction may be carried out by heating the reaction solution at elevated temperatures and preferably at temperatures from about 40° C. to about 150° C. or the reflux temperature of the solvent. The temperature varies depending upon the monomers and other materials present in the reaction solution.

The reaction may also be carried out by subjecting the reaction solution to a UV source to produce the final product. The reaction is carried out for a time sufficient to complete the polymerization, which reaction may proceed for time periods up to about 100 hours or more. The initiators used in the polymerization reaction is dependent upon the type of energy source used and may be different if a UV source is used as opposed to a thermal energy source.

The above monomers of formula (I) may be homopolymerized or they may be copolymerized with suitable comonomers. This copolymerization reaction thus includes the reaction of the quaternary ammonium group-containing organosilicon monomers with one or more comonomers.

The copolymers may contain copolymeric units having the generic structure depicted as -M-. The copolymeric units can be added to achieve the desired physical properties, enhance the solubility in aqueous or nonaqueous media, achieve better miscibility in various solvents or to improve the dispersibility of the polymer.

The first type of M units are represented by styrene and similar vinylaromatics and lower alkenes or alkadienes, such as ethylene, butadiene and the like. The second type of M units are illustrated by vinyl acetamide, vinyl amine, vinyl amine quaternized with hydroxyethylenes or similar water solubilizers or with hydrophobes such as dodecyls, or vinylbenzyl amine quaternized with three long chain alkyl hydrophobes or with three lower alkyl or hydroxyalkyl hydrophiles. Other units include, for example, vinyl acetate, vinyl alcohol, acrylic acid, acrylate and methacrylate esters; acrylamide and acrylamide derivatives, including quaternized acrylamide; N-vinylimidazole and derivatives thereof, including quaternized N-vinylimidazoles; 4-vinylpyridine and derivatives thereof, including quaternized 4-vinylpyridines; N-vinylpyrrolidone and derivatives thereof; vinylbenzyl ethers of polyethylene glycols and their monoalkyl ethers. These units are all known in the art as are the methods for their incorporation into copolymers. Mixtures of two or more M units may, of course, be used.

Generically, the M's can be grouped as 2 to 6 carbon alkylenes or alkenylenes, having pendent therefrom, from 0 to 2 substituent groups selected from aryls, alkaryls, and aralkyls of 6–8 carbons, alkyls of 1–4 carbons, amides, hydroxyls, carboxylic acids, and their esters, nitrogen-containing 5 or 6 atom heterocyclics and amine and ether-substituted aryls, alkaryls and aralkyls.

The M copolymer units may be vinylbenzyl amines quaternized by hydrophilic groups such as hydroxyalkyls of from 1 to 4 carbon atoms, particularly vinylbenzyl amines quaternized with three 2-hydroxyethylenes (i.e. with a triethanolamine structure). Such units are represented structurally as

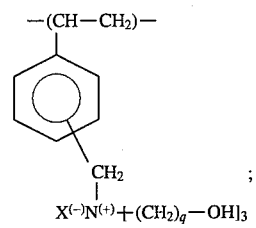

wherein q is 2 through 4 inclusive and most preferably 2.

Another group of copolymer units contemplated herein are vinylbenzyl ethers of poly(ethylene glycol)s or their monoalkyl ethers, particularly methyl ethers. Such units are represented structurally as

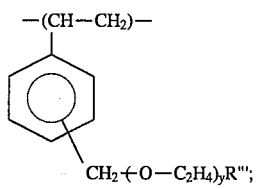

wherein y is 1 through 10 inclusive, preferably 1 through 4 inclusive, and R''' is a hydrogen or lower alkyl unit, such as from 1 to 4 carbons most preferably methyl.

As can be seen from the above, any compatible copolymer unit can be polymerized with the monomers (I) to incorporate the antimicrobial quaternary group-containing organosilicon monomers (I) of the present invention into the polymer structure as long as the monomers do not deleteriously affect the objective purposes of the present invention, which is primarily to achieve antimicrobial effects, for disinfecting contact lenses, etc.

The polymers of the present invention may be crosslinked with various crosslinking agents. Examples of such crosslinking agents are allyl compounds e.g. allyl methacrylate, diallyl itaconate, monoallyl itaconate, diallyl maleate, diallyl fumarate, diallyl succinate, diallyl phthalate, triallyl cyanurate, triallyl isocyanurate, diethylene glycol bis-allyl carbonate, triallyl phosphate, triallyl trimelliate, allyl ether, N,N-diallylmelamine; vinyl compounds, e.g. divinyl benzene, N,N'-methylene bis acrylamide, ethylene glycol dimethacrylate, neopentyglycol dimethacrylate, tetraethylene glycol dimethacrylate, hexamethylene bis maleimide, divinyl urea, bisphenol A bis methacrylate, divinyl adipate, glycerin trimethacrylate, trimethylolpropane triacrylate, trivinyltrimellitate, 1,5-pentadiene, 1,3-bis(4-methacryloxybutyl) tetramethyl disiloxane, divinyl ether and divinyl sulfone; hydroxyl reactive compounds such as polyvalent isocyanates, e.g. hexamethylene diisocyanate, isophorone diisocyanate, toluene diisocyanate; polyaldehydes, e.g. glutaraldehyde and glyoxal; polyacids, e.g. glutaric acid and oxalic acid; polyepoxides, e.g. butane diepoxide, vinylcyclohexane dioxide and butanediol diglycidyl ether; polyols (acid catalysis), e.g. dimethylol urea and diethylene glycol.

The amounts of such crosslinking agents are dependent upon the purpose desired and usually about 0.01 to 10 weight % of the crosslinking agent, based upon the weight of the monomers may be used.

The polymers of the present invention have average molecular weights ranging from about 2,000 to about 1,000,000 for the homo- or co-polymer The average molecular weight as used herein means the weight average molecular weight ($M_w$) as determined by light scattering measurements.

The number of recurring units, i.e. the mers units, ranges from about 10 mers to about 3,000 mers for the quaternary ammonium group-containing organosilicon monomers in the homopolymers or in the case of copolymers, the total number of units of all the comonomers ranges from 10 mers to about 3,000 mers.

The homopolymer of the monomers of the present invention as represented by the polymerized MADAC polymer of Formula (I) above, is expressed by the following formula:

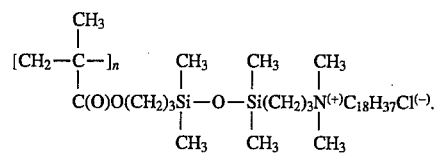

As can be seen from the above, the polymerization takes place at the reactive alkene terminal portion of the MADAC monomer. The n group varies between about 10 mers up to about 3,000 mers as previously mentioned. The comonomers M, similarly react at the alkene portion of the quaternary ammonium group-containing monomer structure.

The polymerization and copolymerization methods discussed above relate to the homopolymerization or copolymerization of the quaternary ammonium group-containing organosilicon monomers, but the monomers may be homopolymerized or copolymerized before being quaternized and then subsequently quaternized. For example, the product as set forth in Step 3 (prior to the quaternizing step), may be polymerized and the resulting polymer subsequently quaternized as in Step 4 for producing the monomer as discussed above.

The polymers of the present invention are primarily used in ophthalmic solutions for cleaning lenses, particularly soft lenses, where penetration of the antimicrobial component into the soft gel structure is to be avoided. However, the liquid composition can be used on hard contact lenses and any surface where antimicrobials and preservatives are typically employed. Further, the polymers of the present invention can be used to produce contact lenses which are strong, flexible, highly oxygen permeable, wettable and optically clear.

To produce solid structures, such as contact lenses, higher molecular weight polymers are employed, especially crosslinked polymers are preferably used, which are crosslinked to a degree sufficient to attain the desirable properties as discussed above. The final lenses thus-produced have sufficient antimicrobial properties to help kill bacteria and other microorganisms which grow on the lenses, but are not toxic or harmful to the eyes.

SPECIFIC EMBODIMENTS

The first three examples will illustrate concrete procedures for producing the antimicrobial polymers of the present invention. These examples are given by illustration only and are not designed to limit the essential inventive concept as broadly disclosed herein.

Example 1

To a dry, 250-milliliter, three-neck flask equipped with a condenser, nitrogen, inlet and magnetic stirrer, was added 10.02 grams 50% 3-methacryloxypropyltetramethyldisiloxanylpropyldimethyloctadecylammonium chloride (MADAC) in methanol, 5.01 grams N,N-dimethylacrylamide, 0.10 grams 2-hydroxy-2-methyl-1-phenylpropan-1-one and 100 milliliters methanol. The mixture was stirred and purged five minutes with nitrogen. The outlets were then sealed and the reaction system subjected to ultraviolet light at ambient temperature for 96 hours. At the end of 96 hours the methanol was removed via rotary evaporation. The residue was purified by stirring in 200 milliliters hexanes for 18 hours. The resulting solids were filtered and the purification process repeated two more times.

Example 2

To a dry, 250-milliliter, three-neck, water-jacketed flask equipped with a condenser, nitrogen, inlet, magnetic stirrer and constant-temperature water circulator, was added 10.02 grams 50% 3-methacryloxypropyltetramethyldisiloxanylpropyldimethyloctadecylammonium chloride (MADAC) in methanol, 5.06 grams N,N-dimethylacrylamide, 0.12 grams Vazo 52 (pentanenitrile,2,4-dimethyl, 2,2-azobis) and 100 milliliters methanol. The mixture was stirred and purged five minutes with nitrogen. The outlets were then sealed and the reaction system heated to 60° C. for 96 hours. At the end of the reaction, the methanol was removed via rotary evaporation. The residue is stirred in 200 milliliters hexanes for 18 hours. The resulting solids were filtered and the purification process repeated for two additional steps.

Example 3

To a dry 250-milliliter, three-neck water-jacketed flask equipped with a condenser, nitrogen, inlet, magnetic stirrer and constant-temperature water circulator was added 10.03 grams 50% 3-methacryloxypropyltetramethyldisiloxanylpropyldimethyloctadecylammonium chloride (MADAC) in methanol, 5.03 grams n-vinyl pyrrolidone, 0.10 grams Vazo 52 and 100 milliliters methanol. The mixture was stirred and purged five minutes with nitrogen. The outlets were then sealed and the reaction system heated to 60° C. for 96 hours. At the end of the reaction, the methanol was removed via rotary evaporation. The residue is stirred in 200 milliliters hexanes for 18 hours. The resulting solids were filtered and the purification process repeated two additional steps.

ANTIMICROBIAL TESTING

The following Examples 4–6 represent examples in which the solutions of the polymers of Examples 1–3 were tested for their preservative efficacy and cytotoxicity. The formulations and results are shown in Tables 1 and 2, respectively.

Examples 4–6

Solutions were prepared from the polymers described in Examples 1 through 3. Table 1 indicates the concentration of each solution and solvent. Each solution was tested for preservative efficacy and cytotoxicity. The results of the microbial and toxicity tests were shown in Table 2.

TABLE 1

| Formulations Examples 4–6 | | | |
|---|---|---|---|
| Example | Polymer Used | Concentration | Solvent |
| 4 | Example 1 | .025% | Saline, Isotonic |
| 5 | Example 2 | .025% | Saline, Isotonic |
| 6 | Example 3 | .025% | Saline, Isotonic |

TABLE 2

| Cytotoxicity and Preservative Tests Results | | | | | |
|---|---|---|---|---|---|
| | | Pseudomonas[1] Aeruginosa | | Aspergillus[1] Fumigatus | |
| Example | Cytotoxicity | 24 Hours | 7 Days | 24 Hours | 7 Days |
| 4 | Negative | Negative | Negative | $10^3$ | $10^3$ |
| 5 | Negative | Negative | Negative | $10^3$ | $10^3$ |
| 6 | Negative | Negative | Negative | $10^3$ | $10^3$ |

[1]Initial inoculum was $10^6$ for all tests.

CONTACT LENSES PRODUCED FROM THE ANTIMICROBIAL POLYMERS OF THE PRESENT INVENTION

Example 7 below illustrates a typical procedure for preparing contact lenses from the quaternary ammonium group-containing organosilicon monomers of the present invention.

Example 7

Contact lenses were prepared from the following formulation: 9.85 grams 2-hydroxyethyl methacrylate, 0.05 grams ethyleneglycol dimethacrylate, 0.10 grams 3-methacryloxypropyltetramethyldisiloxanylpropyldimethyloctadecylammonium chloride (MADAC) and 0.05 grams 2-hydroxy-2-methyl-1-phenyl-propan-1-one. The formulation was stirred to effect solution and cured via actinic irradiation. After a two-hour cure, the resulting lenses were clear and colorless.

The aqueous solutions for disinfecting soft contact lenses provided herein are compatible, from pharmacological and chemical standpoints, with typical ingredients normally included in the antimicrobial or disinfectant solutions for contact lens care, and do not significantly alter the toxicity of the system. They have very low mammalian toxicity and are chemically stable, odorless and non-volatile, and exhibit a broad spectrum of anti-bacterial activity against a wide range of microorganisms which pose a danger to the eye, as exemplified by Pseudomonas aeruginosa. They are nontoxic and non-irritating to the tissues of the eye in the concentrations and frequency of use contemplated herein.

The compositions of this invention also are compatible with other ingredients usually found in ophthalmological eye care solutions. They are easily handled and applied, do not foam, and can be and are chemically stable in a wide range of pH's. However, it is preferable to apply the solutions at a pH of 7, plus or minus one unit, and in an isotonic solution, so that there will be no adverse effects to the eye from osmotic pressure due to an imbalance in the ionic strength of the solution.

In the practice of the present invention, in respect to the sterilization of contact lenses, the active quaternary ammonium group-containing organosilicon polymer is present in the solution in amounts sufficient impart antimicrobial or disinfecting properties to the solution against pathogens, i.e. in an amount sufficient to destroy or inhibit multiplication of bacterial microorganisms such as *Staphylococcus aureus, Escherichia coli, Pseudomonas aeruginosa,* and *Aerobacter aerogenes,* while at the same time not causing irritation to the eye or damage to the lens.

The antimicrobial polymers of the present invention may be present in small amounts such as 0.001 weight %, based on the weight of the aqueous disinfectant solution, when used as a disinfectant to clean hard surfaces, such as contact lenses. The upper limit is dictated by factors which may cause eye irritation over long periods of time and/or damage to the soft contact lenses, when used for that purpose. An upper limit is about 0.5 weight %, but a practical range is from about 0.002 weight percent to about 0.1 weight % based upon the weight of the aqueous disinfectant solution.

A typical disinfectant solution useful in the practice of this invention, may contain in addition to the active ingredient, buffers, stabilizers, and isotonic agents. These additional materials should be non-toxic and should not distort or otherwise damage the soft lens and they should not lower or raise the pH below 5.5. or above 8.5 since this can have an adverse effect on occular tissue.

Other disinfectants can be used in the disinfectant composition to enhance the sterilizing or disinfecting effects, if desired.

The disinfectant liquid compositions of the present invention can be used in a variety of compositions where the antimicrobial effects of the polymer are desired. The description of the utilities in the specification and claims should therefore not be construed as precluding the utility of such compositions or polymers in areas or fields of uses other than specifically described herein.

What is claimed is:

1. An antimicrobial quaternary ammonium group-containing monomer of the formula:

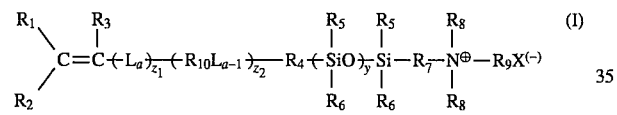

wherein $R_1$, $R_2$ and $R_3$ are independently H, $C_{1-7}$ alkyl, or $-COOR^{13}$ with $R^{13}$ being H or $C_{1-4}$ alkyl;

$Z_1$ and $Z_2$ are independently 0 or 1;

$L_a$ is

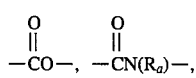

or a direct bond;

$L_{a-1}$ is a direct bond

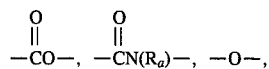

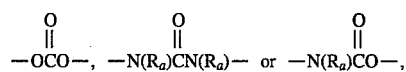

wherein $R_a$ is H or $C_1$–$C_8$ alkyl;

$R_{10}$ is $C_{1-20}$ aliphatic, $C_{1-25}$ cycloaliphatic or $C_{1-20}$ aryl, each of which may be substituted with up to five halogen atoms, or $(CH_2CH(R_aO)_j$ where j is from 1 up to 50 and $R_a$ is as defined above;

$R_4$ and $R_7$ are independently $C_{2-10}$ aliphatic, $C_{2-8}$ alkylene, $C_{1-4}$ alkylene-(oxy-$C_{1-4}$ alkylene)$_g$, $C_{1-4}$ alkylene(–)OCH$_2$-(hydroxy $C_{1-4}$ alkylene)-CH$_2$, cycloaliphatic up to 25 carbon atoms or aryl up to 25 carbon atoms, wherein g is an integer from 1 to 10;

y is an integer of 1 to 10;

$R_5$ and $R_6$ are independently $C_1$–$C_8$ alkyl, $C_6$–$C_{25}$ aryl, or $C_6$–$C_{25}$ cycloaliphatic which may be substituted by one or more halogen, hydroxy, $C_{1-4}$alkyl, carboxy or $C_{1-12}$ perhaloalkyl groups and $R_5$ or $R_6$ may be —Si(OSiCH$_3$)$_3$;

$R_8$ and $R_9$ are independently $C_1$–$C_{24}$ alkyl, $C_{1-24}$ alkylene, $C_3$–$C_{24}$ cycloaliphatic and $C_{6-25}$ aryl, which groups may be each substituted with from 1–11 groups selected from hydroxy, $C_{1-4}$alkyl, carboxy, $C_{1-12}$ perhaloalkyl or halogen and $R_8$ and $R_9$ may also be $(CH_2CH_2O)_xH$, where x is from 1 to 10 units, and X is an ophthalmically acceptable counterion.

2. An antimicrobial monomer according to claim 1 of the formula:

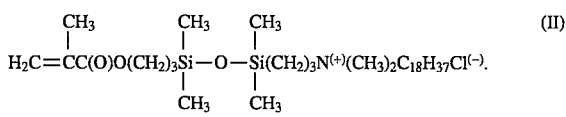

3. An antimicrobial monomer according to claim 1 of the formula:

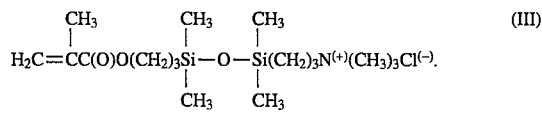

4. An antimicrobial monomer according to claim 1 of the formula:

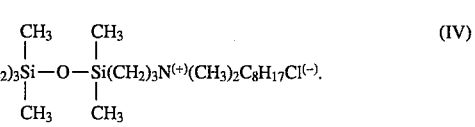

5. An antimicrobial monomer according to claim 1 of the formula:

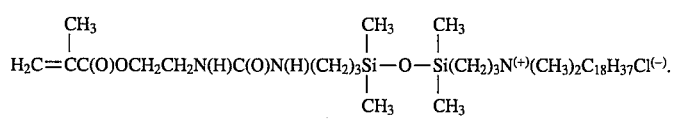

6. A method producing an antimicrobial monomer of the formula:

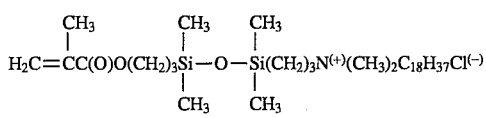

by (1) reacting a compound of the formula:

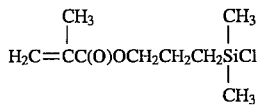

with a compound of the formula:

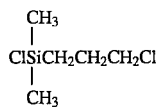

in the presence of water to produce a compound of the formula:

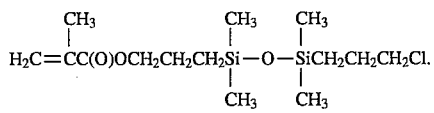

(2) reacting the compound of the formula (IIC) with an excess of $NH_3$ to produce a compound of the formula:

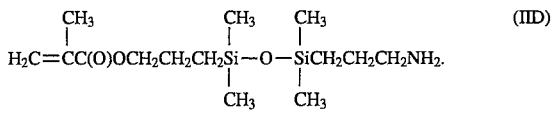

(3) reacting said compound of the formula (IID) with an excess of $CH_3Br$ to produce a compound of the formula:

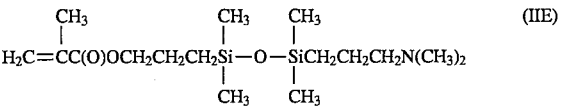

and;

(4) quaternizing the compound of the formula a quaternizing ammonium agent of the formula (IIE) with $CH_{18}H_{37}Cl$.

* * * * *